United States Patent [19]

Lavallee et al.

[11] Patent Number: 4,783,529

[45] Date of Patent: Nov. 8, 1988

[54] RAPID SYNTHESIS OF RADIOLABELED PORPHYRIN COMPLEXES FOR MEDICAL APPLICATION

[75] Inventors: David K. Lavallee, Croton-On-Hudson, N.Y.; Daniel Mansuy, Paris; Jean-Paul Battioni, Massy, both of France

[73] Assignee: Research Corporation Technologies, New York, N.Y.

[21] Appl. No.: 804,218

[22] Filed: Dec. 3, 1985

[51] Int. Cl.[4] ............................................. C07D 487/22
[52] U.S. Cl. ..................................... 540/145; 424/1.1
[58] Field of Search .......................................... 540/149

[56] References Cited

PUBLICATIONS

Callot et al, JACS, vol. 104 (1982) pp. 1272–1276.
Dolphin et al, Inorganic Chemistry, vol. 20 (1981) pp. 4348–4351.

*Primary Examiner*—Richard L. Raymond
*Attorney, Agent, or Firm*—Scully, Scott, Murphy & Presser

[57] ABSTRACT

This invention relates to a novel method for the rapid synthesis of radiolabeled porphyrin complexes which are highly useful for biomedical application, i.e. conjugation to protein antibodies for use in tumor imaging and internal radiation therapy.

16 Claims, No Drawings

RAPID SYNTHESIS OF RADIOLABELED PORPHYRIN COMPLEXES FOR MEDICAL APPLICATION

This invention relates to a new and rapid synthesis of radiolabeled porphyrin complexes for medical application.

BACKGROUND OF THE INVENTION

The use of radioactively labeled diagnostic and therapeutic agents have become routine practice in clinical and analytical laboratories throughout the world. Such radioactively labeled compounds are used both in vitro, for example, in radioimmunoassay systems, and in vivo, for example, both in diagnostic imaging techniques and in radiation therapy techniques.

Initially, the number of radioisotopes that could be firmly attached to the typical organic molecules used as diagnostic and therapeutic agents was limited. The difficulty in forming stable carbon-metal bonds prevented the early utilization of many radioactive metals and typically limited radioisotopes used to label organic molecules to isotopes of phosphorus, carbon, hydrogen and iodine.

Recently, a new approach has enabled the labeling of such agents with metal ions. In this approach a chelating moiety is covalently attached to the molecule of interest, and a radioactive ion is then chelated by the sequestering groups of the chelator. Typical chelating moieties which have been used for this purpose in the prior art have been analogues or derivatives of ethylenediaminetetraacetic acid (EDTA), although many variations have also occurred.

Attempts to "mark" or "tag" cancer cells in order to differentiate them from normal tissue have been extensively investigated. Various fluorescent compounds such as tetracycline derivatives, acridine dyes and porphyrin compounds have been tried with mixed results. Of these, porphyrin compounds have shown remarkable affinity for neoplastic tissues.

Porphyrins and related analogs are complex tetrapyrrole compounds normally found in plants and in animals. They perform many vital biological functions by combining with metallic ions such as iron, magnesium, manganese, zinc, etc. to form metalloporphyrins. Metalloporphyrins are essential for the normal metabolism of plants and animals. Many of these compounds exhibit strong fluorescence when exposed to an appropriate exciting light source.

The preferential affinity of porphyrin compounds for various type of neoplasms has been known for more than four decades. When injected intravenously into tumor-bearing animals, a brilliant red-orange fluorescence is produced by ultra violet light activation of the porphyrin accumulated in the tumor.

Various porphyrin compounds have been labeled with radionuclides such as $^{64}$Cu and $^{57}$Co. Protoporphyrin and hematoporphyrin, an artificial porphyrin prepared by treating hemoglobin with concentrated sulfuric acid, labeled with $^{64}$Cu have been shown to concentrate in mouse tumors.

The common method of labeling porphyrins with radionuclides involves the reflux reaction of a porphyrin with a radioactive metallic salt in an acidic or basic medium. Dilute hydrochlorice acid, acetic acid or dilute base such as sodium hydroxide is used to dissolve the porphyrin and to act as the reaction medium. An aqueous solution of cobaltous chloride ($^{57}$CoCl$_2$), cuprous chloride ($^{64}$CuCl$_2$) or $^{64}$Cu-acetate is added to the porphyrin solution and refluxed for 30 minutes to up to 24–48 hours depending on the reactivity of the porphyrin used in the labeling process. The pH of the radioactive admixture is then adjusted to 6–8 whenever possible without causing denaturation or precipitation of the radiolabeled porphyrin. In many instances, the labeled product must remain in either acidic or basic condition in order to insure chemical and labeling stability.

Although the labeling process is quite simple, the labeling yield is unsatisfactory, ranging from 10–40%. The final labeled product contains many radioactive impurities. These include free or unbound radionuclide, denatured by-products and insoluble radiocolloids in the form of hydroxides such as $^{57}$Co(OH)$_2$ or $^{64}$Cu(OH)$_2$. Without extensive purification processes, these preparations are not useful or suitable for medical applications.

BRIEF SUMMARY OF THE INVENTION

The present invention relates to the preparation of radiolabeled porphyrin complexes useful for biomedical application, i.e. conjugation to protein antibodies for use in tumor imaging and internal radiation therapy.

The present invention is based upon the discovery that it has been found that N-benzylporphyrins react very rapidly in organic and aqueous solutions to form non-N-substituted radiolabeled metalloporphyrins. Specifically, the N-substituted porphyrins complex with metal ions as much as $10^5$ times faster than the corresponding non-N-substituted porphyrins. The N-substituent of these complexes can be readily removed to produce the non-N-substituted metalloporphyrin. The present invention thus provides products which are eminently suitable for medical application as compared to the prior art. The improved method of this invention involves the use of diphenylbenzylsulfonium salts, e.g., diphenyl-p-nitrobenzylsulfonium tetrafluoroborate, to form the N-benzyl-substituted prophyrin. The resulting product is stable in the absence of metal ions but incorporates metal ions very rapidly under mild conditions.

The present invention readily permits the rapid incorporation of metals into porphyrins conjugated to proteins. The radionuclides may be readily attached to monoclonal antibodies and antibody fragments for utilization in tumor imaging and internal radiation therapy.

DETAILED DESCRIPTION OF THE INVENTION

In carrying out the present invention, a naturally derived porphyrin, e.g., protoporphyrin, deuteroporphyrin or hematoporphyrin or one of the synthetic porphyrins described hereinafter is reacted with benzyldiphenylsulfonium tetrafluoroborate. The N-benzyl group is added almost quantitatively when refluxed overnight in dichloromethane under stoichiometric conditions. This reaction is illustrated schematically below using 5,10,15,20-tetrakis(4-methylcarboxyphenyl)porphyrin which is prepared by standard techniques from 4-formylmethylbenzoate and pyrrole.

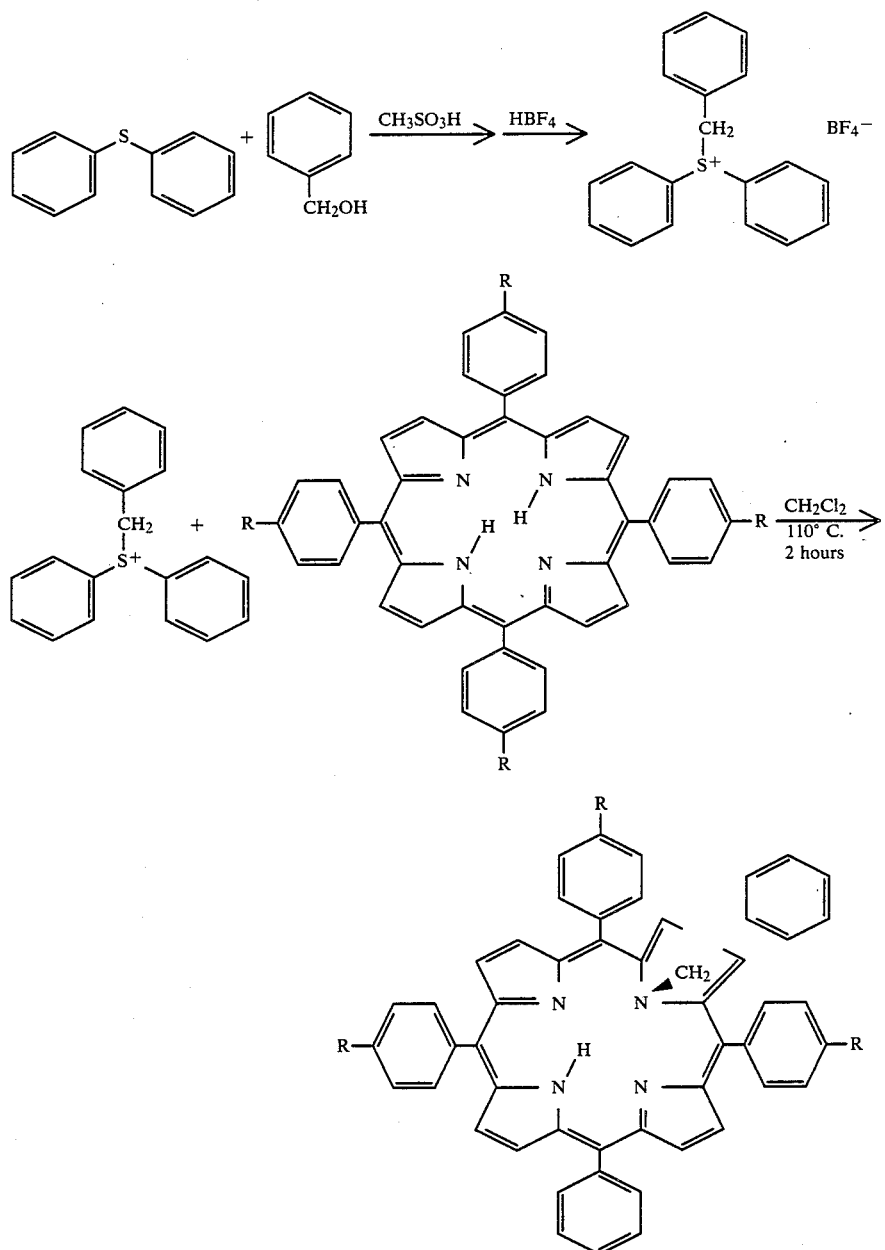

wherein R is carboxy. The resulting product is N-benzyl-5,10,15,20-tetrakis(4-carboxyphenyl)porphyrin, in itself a new product.

A wide variety of alkyl or aryl diphenylsulfonium salts prepared according to the method of Badet and Julia, Badet, B. and Julia, M. (1979), Preparation Aisee de Sels de Sulfonium, *Tetrahedron Lett.* 1101–1104, and which is incorporated herein by reference, may be used.

As indicated earlier, the resulting N-benzylporphyrin is capable of forming metal complexes much more rapidly than the corresponding non-N-substituted porphyrins. In general, any of the metals of Groups 8 and 9 may be used. We have found that both cold and radioisotopes of copper ($^{64}Cu$ and $^{67}Cu$), cobalt ($^{57}Co$), nickel ($^{63}Ni$) and palladium ($^{109}Pd$) are readily incorporated into the porphyrin. The resulting metalloporphyrins are useful for rapidly labeling antibodies with gamma emitting isotopes for medical imaging.

Both the free base and esters of N-benzylprotoporphyrin, N-benzyldeuteroporphyrin and N-benzylhematoporphyrin may be used in the metalation reaction.

After the Cu(II) ion is bound, however, the N-substituent must be removed to give a highly stable porphyrin complex since metal ions are readily removed from the N-substituted metalloporphyrins. Simple N-substituents such as the methyl group are not removed by water as a nucleophile under mild conditions, but require such strong nucleophiles as amines. The strong nucleophiles necessary to remove the N-methyl substituent require reaction conditions too harsh to be used for porphyrin-antibody-conjugates. The N-benzyl substituents are more easily removed. The rate for the overall reaction of metal complexation and N-benzyl group removal in buffered aqueous solution is rapid and, importantly, independent of Cu(II) concentration.

The metalation reaction mechanism for the N-benzyl porphyrins is illustrated schematically below:

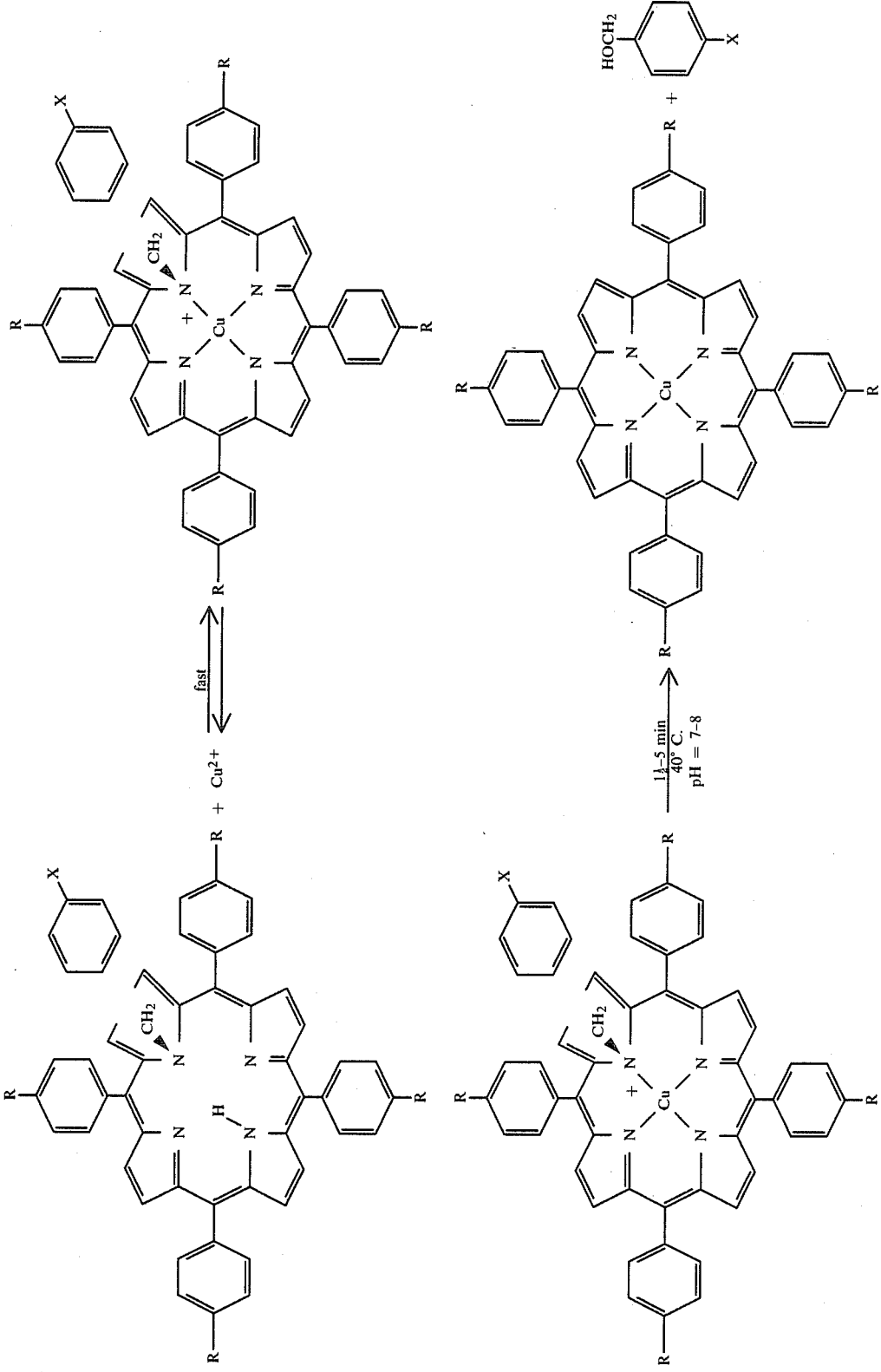

wherein R is preferably CO₂H or SO₃H and X is H or NO₂.

In general, N-benzylporphyrins of the following formula may be used in the metalation reaction:

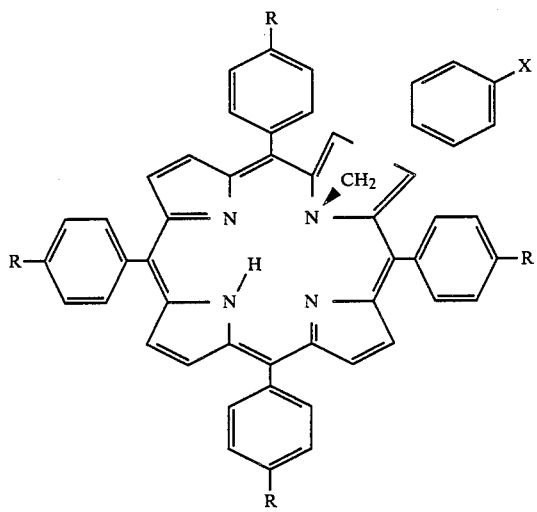

wherein X is hydrogen, nitro, hydroxy, lower alkyl ($C_1$–$C_4$), or lower alkoxy ($C_1$–$C_4$) and R is carboxy or sulfonato.

As indicated above, the present invention also includes the following new compounds, the synthesis of typical porphyrins of this invention being described hereinafter: free bases and dimethyl esters of N-benzylhematoporphyrin, N-benzylprotoporphyrin, N-benzyldeuteroporphyrin, and in addition N-benzyl-5,10,15,20-tetrakis(4-carboxyphenyl)porphyrin and N-4-nitrobenzyl-5(4-carboxyphenyl)-10,15,20-tris(4-sulfophenyl)-porphyrin.

The structures of the novel compounds N-benzyl-5,10,15,20-tekrakis(4-carboxyphenyl)porphyrin N-bzHTCPP, and of N-4-nitrobenzyl-5(4-carboxyphenyl)10,15,20-tris(4-sulfophenyl)porphyrin, N-bzHCS₃P are shown below:

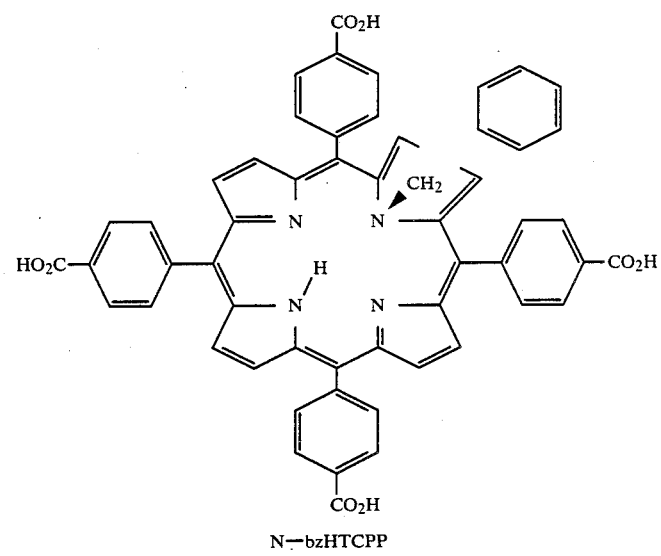

N—bzHTCPP

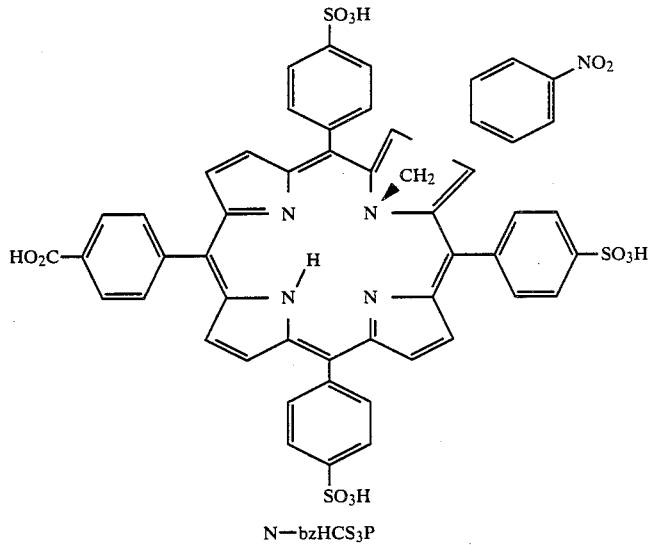

N—bzHCS₃P

The synthesis of the novel compound N-4-nitrobenzyl-5(4-carboxyphenyl)-10,15,20-tris(4-sulfophenyl)-porphyrin is illustrated schematically below:

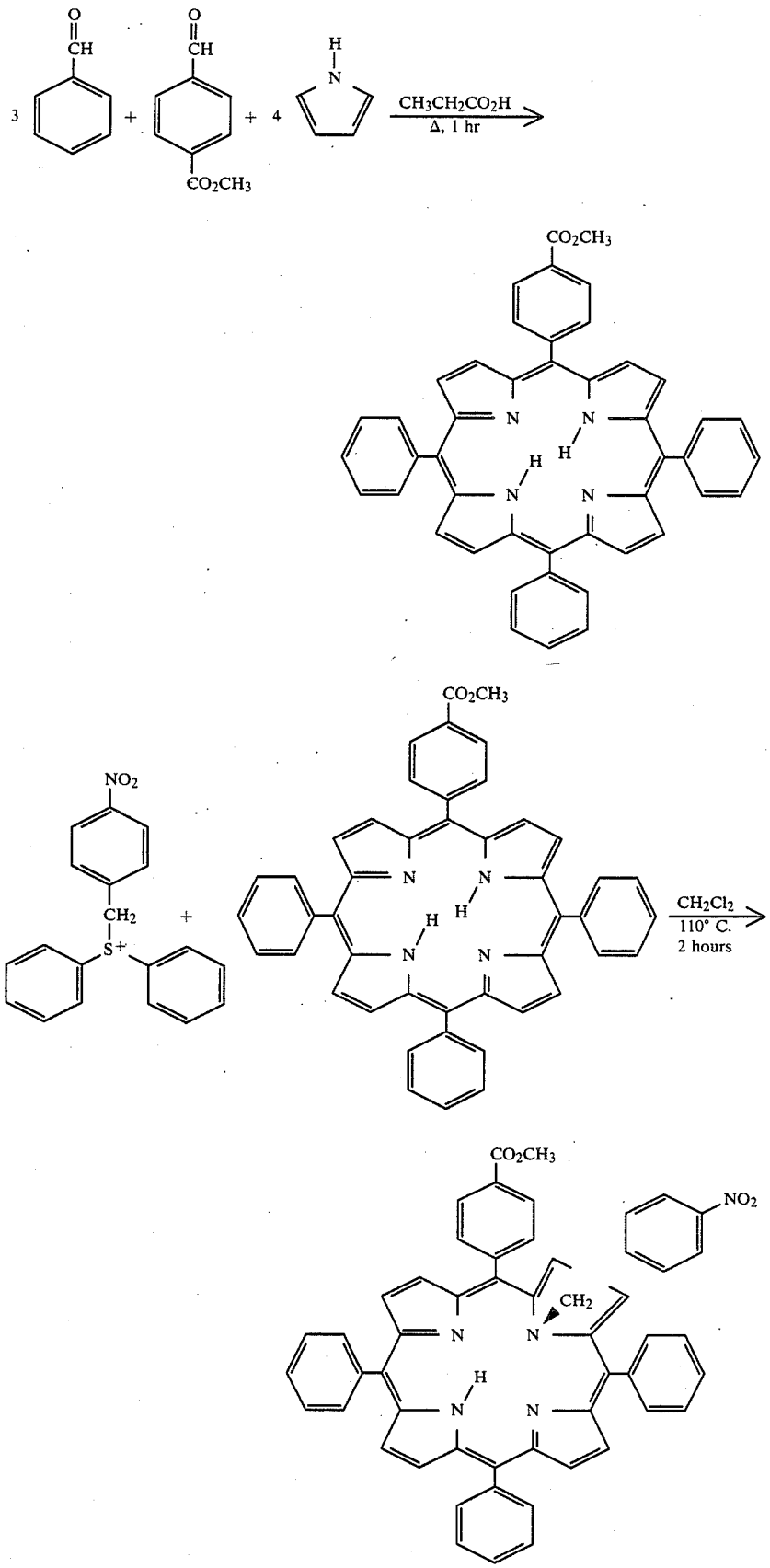

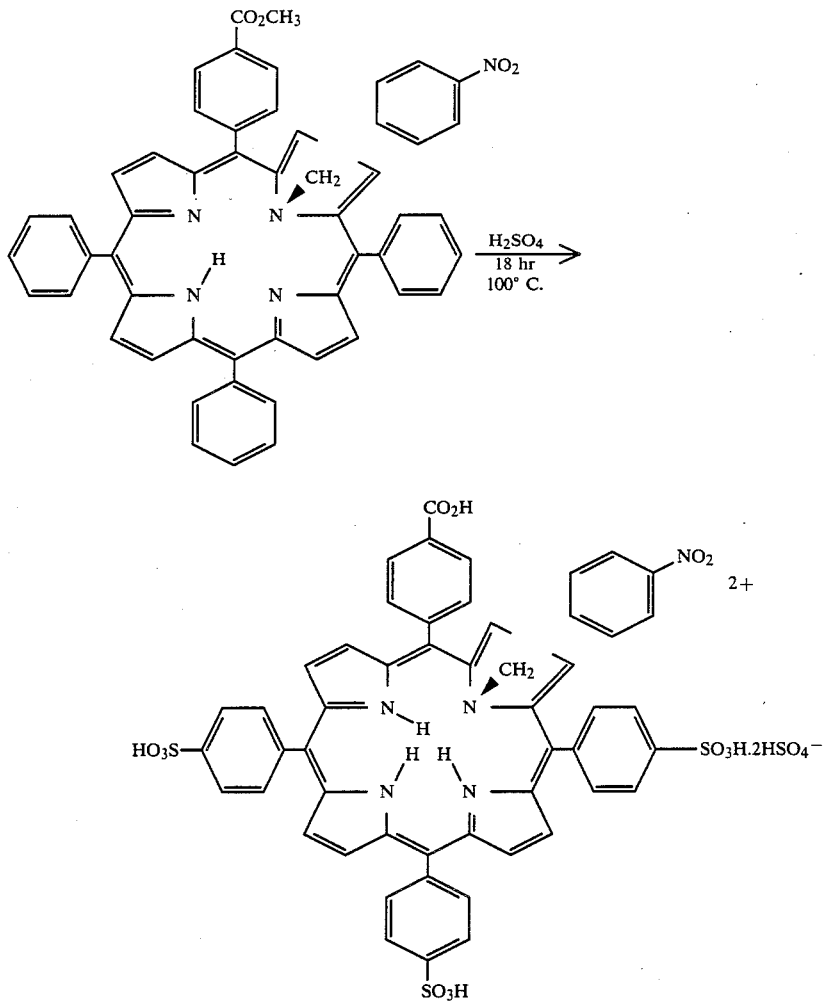

The conjugation of the N-benzylporphyrins of this invention to antibodies, e.g. immunoglobulin G(IgG), may be readily carried out in the manner described hereinafter. N-4-nitrobenzyl-5-(4-carboxyphenyl)-10,15,20-tris(4-sulfophenyl)porphyrin, N-benzyl-5,10,15,20-tetrakis(4-carboxyphenyl)porphyrin as well as other N-benzylporphyrins enumerated hereinabove may be successfully bound to antibodies using the following general procedure:

The preferred method involves the formation of an activated carboxylate of the N-benzylporphyrin by reaction with N-hydroxysuccinimide in the presence of 1-ethyl-3-(3-dimethylaminopropyl)carbodiimide hydrochloride, followed by conjugation with IgG. A 1:10:10:10 molar ratio of IgG/EDAC/NHS/N-benzylporphyrin works favorably for the conjugation. Metalation of the N-benzylporphyrin, accompanied by loss of the N-benzyl group to form the $^{67}$Cu labeled porphyrin-IgG conjugate is readily accomplished with $^{67}$CuCl$_2$ in 30 minutes at 40° C. in aqueous borate buffered solution at pH of 8.5. Thus the attachment of the N-benzylporphyrin to antibodies followed by rapid metalation with radiocopper provides an effective method to radiolabel antibodies with copper.

The invention will be described in greater detail in conjunction with the following specific examples.

EXAMPLE 1

Benzyldiphenylsulfonium tetrafluoroborate

Benzyldiphenylsulfonium tetrafluoroborate was prepared according to the procedure described by Badet and Julia supra by deaerating 0.10 mole of diphenylsulfide with Ar. 0.15 Mole of benzyl alcohol was slowly added with continued Ar flow and the solution was cooled with an ice bath. When the temperature reached 5° C., 0.30 mole of methanesulfonic acid was added drop by drop. The Ar flow was stopped and the mixture, now milky-white, was stirred and allowed to come to room temperature. After 3 hours the mixture was washed with 3 100 mL portions of 4:1 diethylether/hexane solution. The residue was cooled in an ice bath and 20 mL of H$_2$O was added slowly, followed by drop-by-drop addition of 30 mL of 46% HBF$_4$. The mixture was allowed to come to room temperature and stirred for 30 min. Then 3 100 mL portions of CH$_2$Cl$_2$, were used to extract the product and about 30 mL of a saturated solution of sodium bicarbonate was added, making the solution slightly alkaline. After about 25 g of MgSO$_4$ had been used to dry the solution, it was filtered and reduced in volume using a rotary evaporation. About 50 mL of methanol was added followed by addition of diethylether to cause precipitation (350–400 mL). The white crystals were filtered, washed with diethyl ether and air dried. Yield 8.6 g (24%), mp 107°–108° C.

N-benzylprotoporphyrin IX Dimethyl Ester

Two methods were employed for the preparation of this compound. In the first, protoporphyrin IX dimethyl ester was combined with a 10% excess of benzyldiphenylsulfonium tetrafluoroborate (typically $10^{-3}$ to $10^{-2}$M) in dichloromethane and stirred at room temperature overnight. In the second, the reagents were combined at the same relative amounts at a high concentration ($10^{-2}$M or over) in $CH_2Cl_2$ in a glass tube with a Teflon stopper and heated at 105°–120° C. using an oil bath for two hours. In each case, the reaction mixtures were neutralized with 1M aqueous ammonia. Isolated yields of 90% were obtained after column chromatography on silica using $CH_2Cl_2$ as eluent. In the case of the second method, the reaction typically appears to be quantitative by visible-uv spectrometry and TLC. The visible-uv spectrum of N-benzylprotoporphyrin IX dimethyl ester is similar to that of N-alkylprotoporphyrins 417 nm ($1.0 \times 10^5 M^{-1} cm^{-1}$), 511 nm($1.1 \times 10^4 M^{-1} cm^{-1}$), 544 nm ($6.7 \times 10^3 M^{-1} cm^{-1}$), 593 nm ($4.5 \times 10^3 M^{-1} cm^{-1}$), 627 nm ($2.2 \times 10^3 M^{-1} cm^{-1}$) and 651 nm ($2.6 \times 10^3 M^{-1}$). The $^1$H nmr spectrum in $C_6D_5N$ shows the characteristic upfield shift of the N-methylene hydrogen atoms (a pattern of 4 doublets of doublets between 4 and 4.44 ppm upfield from TMS, J=15.3 Hz) and the phenyl ring protons are strongly shifted (o at 4.5 ppm, m and p in a complex set with vinyl proton resonances between 6.0 and 6.8 ppm). The mass spectrum shows the parent peak +1 and +2 at 682 and 683 m/e.

N-benzylhematoporphyrin IX Sodium Salt

The N-benzylprotoporphyrin IX dimethyl ester was converted to corresponding 2,4-bis(1-hydroxyethyl)-porphyrin in the free acid form by acid hydrolysis using 30% HBr in acetic acid. 300 mg of the starting material was dissolved in 40 ml of 30% HBr in acetic acid, stirred 24 hr, then 50 ml 5% v/v aqueous HCl were added and the mixture was stirred for 24 hrs.

EXAMPLE 2

N-benzyl-5,10,15,20-tetraphenylporphyrin

This compound was synthesized using tetraphenylporphyrin as described for N-benzylprotoporphyrin IX dimethyl ester, but alumina was used for the column chromatography. The visible-uv absorption spectrum was very similar to that of N-methyltetraphenylporphyrin and, as expected, N-p-nitrobenzyltetraphenylporphyrin 434 nm, ($3.9 \times 10^5 M^{-1} cm^{-1}$), 533 nm, ($1.3 \times 10^4 M^{-1} cm^{-1}$) 573 nm, ($2.2 \times 10^4 M^{-1} cm^{-1}$) 615 nm, ($7.1 \times 10^3 M^{-1} cm^{-1}$), 675 nm, ($6.6 \times 10^3 M^{-1} cm^{-1}$). The $^1$H nmr spectrum in $CDCl_3$ showed the typical upfield shift of the N-methyl protons (at 3.38 ppm upfield from TMS) with phenyl peaks at 4.6 ppm (o), 6.5 ppm(m) and 6.7 ppm(p) and b-pyrrolic hydrogen resonances at 7.6 ppm (s, 2H), 8.5 ppm (d, 2H), 8.6 ppm(d, 2H) and 8.9 ppm (s, 2H). Anal. for $C_{51}H_{36}N_4.1/4CH_2Cl_2$ Calc. 84.78% C, 5.07% H, 7.71% N, 2.44% Cl; Found. 84.86% C, 5.29% H, 7.65% N, 2.15% Cl.

EXAMPLE 3

N-benzyl-5,10,15,20-tetrakis(p-carboxyphenyl)porphyrin 5,10,15,20-tetrakis(p-methylcarboxyphenyl)porphyrin precursor was synthesized from p-formylmethylbenzoate and freshly distilled pyrrole, each 0.35M in refluxing propionic acid. This porphyrin and benzyldiphenylsulfonium tetrafluoroborate were combined in equimolar amounts (0.015M) in dichloromethane and stirred overnight. The resulting green solution was neutralized with 1M aqueous ammonia, extracted with $H_2O$ and chromatographed on alumina with $CH_2Cl_2$ as eluent. The purple solution gives a green band on the column (preceded by a small pink band of unreacted $H_2TPP$) which elutes as a purple solution, as in the case of N-bzHTPP. The ester is converted to the corresponding carboxylate by dissolution in warm THF, addition of an equal volume of 5M aqueous KOH and stirring overnight. In the resulting mixture, the purple aqueous layer contains the porphyrin and the THF layer is nearly colorless. The aqueous layer was removed, cooled using an ice bath and carefully neutralized with 1M HCl until precipitation occurred (about pH 4). The precipitate was filtered with a medium porposity fritted glass funnel, washed throughly with water and air-dried. Visible-uv spectrum of the methyl ester: 678 nm ($4.61 \times 10^3$), 618 nm (sh), 578 nm ($1.33 \times 10^4$), 536 nm ($9.16 \times 10^3$), 437 nm ($1.91 \times 10^5$); free acid in alkaline $CH_3OH$, 676 nm ($6.16 \times 10^3$), 618 nm (sh), 578 nm ($1.71 \times 10^4$), 536 nm ($1.01 \times 10^4$), 431 nm ($1.52 \times 10^5$); free acid in aqueous 3M NaOH, 695 nm ($6.08 \times 10^3$), 604 nm ($1.81 \times 10^4$), 439 nm ($1.65 \times 10^5$). Anal. for $C_{55}H_{36}N_4O_8.HCl.4H_2O$ Calc. 66.8% C, 4.54% H, 5.66% N, 3.53% Cl; Found: 67.3% C, 4.20% H, 5.41% N, 2.67% N, 2.67% Cl.

EXAMPLE 4

Formation of Cu(II). Co(III). Pd(II) and Ni(II) Complexes of Protoporphyrin IX Dimethyl Ester. Hematoporphyrin and Tetraphenylporphyrin The N-benzyl porphyrin was dissolved in boiling methanol at $10^{-3}$ to $10^{-2}$M and a 2-fold excess of the appropriate metal chloride salt added (potassium tetrachloropalladate) in the case of Pd(II)). Aliquots were withdrawn periodically and immediately cooled to quench the reaction. In the case of Co(II), initial spectra indicated formation of diprotonated N-benzylporphyrin so the non-coordinating base 2,2,6,6-tetramethylpiperidine was added after addition of $CoCl_2.6H_2O$ (about 50 L of base/100 ml of methanol). The reactions of Cu(II), Co(II), Ni and Pd(II) were complete (as indicated by visible-uv spectrometry) in less than 5 minutes. Completion of the reaction with Ni(II) required 20 minutes. The reactions appear to be nearly quantitative by visible spectroscopy and after extraction using $CH_2Cl_2$ and water (to remove the unreacted metal salts) filtration and crystallization using acetonitrile/$CH_2Cl_2$ yields were 90–95% for 50 mg scale preparations. Reactions with N-benzyltetrakis(p-carboxyphenyl)porphyrin were carried out in aqueous solution, 0.1M acetate buffer at pH 6, at 90° C. using a two-fold excess of metal salt. Reactions were complete according to visible spectra in ten minutes. Products were obtained in nearly quantitative yield (95%) by acidification of the solution of pH 3–4 with acetic acid, isolation on a medium porosity glass fritted funnel, thorough washing with water and air drying. Each of these metal complexes gives a single spot with an $R_f$ difference of 0.4–0.6 from the free porphyrin on silica TLC plates using acidic (HCl) CH$_3$OH. All products showed expected visible-uv spectra (Co(TPP)Cl, CuTPP, PdTPP, CoPP, CuPP(DME), PdHP. The spectra of CuTPPC$_4$, PdTPPC$_4$ and CoTPPC$_4$Cl closely resemble those reported for corresponding TPP complexes as expected (in alkaline CH$_3$OH, CuTPPC$_4$: 413 nm (1.34×10$^5$), 538 nm 7.06×10$^3$; PdTPPC$_4$: 415 nm (1.43×10$^5$), 522 nm (1.43×10$^4$); CoTPPC$_4$Cl: 430 nm (1.30×10$^5$) 547 nm (1.06×10$^4$)).

EXAMPLE 5

N-p-nitrobenzyl-5-(p-carboxyphenyl)-10,15,20-tris(p-sulfophenyl)porphyrin 5-(p-methylcarboxyphenyl)10,15,20-triphenylporphyrin, (1)

Benzaldehyde (20.0 mL, 0.20 mol) and methyl-p-formylcarboxybenzaldehyde (10.8 g, 0.66 mol) were mixed and added slowly to a refluxing solution of pyrrole (19.0 mL, 0.27 mol) in propionic acid (1.0 L). Careful addition is necessary to prevent overheating and loss of material. After 1 h of reflux, the solution was allowed to cool to about 60° C. and an equal volume of ethylene glycol was added. The reaction mixture was chilled overnight using an ice bath. Filtration with a medium porosity glass fritted funnel gave 4.5 g (9%) of crude product. After a cold methanol wash, the product was air dried. To achieve good chromatographic separation, the ester was hydrolyzed using equal volumes of aqueous 4.0M NaOH and THF with stirring overnight. After removal of solvent using a rotary flash evaporator, the free acid was purified using flash chromatography. The first band, eluted with CH$_2$Cl$_2$, was H$_2$TPP and comprised the bulk of the product. The second band, eluted with CH$_2$Cl$_2$ containing 0.25% ethanol, was the nonmethylcarboxyphenyl product (0.55 g, 1% overall yield). Separation was also effected on preparative TLC plates. The visible-uv spectrum in CH$_2$Cl$_2$ (with the logarithm of the molar absorptivities in parentheses) is: 646 nm (3.61); 590 nm (3.71); 550 nm (3.88); 515 nm (4.23), 485 nm (3.54), 423 nm (5.16), 414 nm (5.17) and 374 nm (4.30). The ester was hydrolyzed with a mixture of equal volumes of 4.0M NaOH and THF. Anal. for C$_{45}$H$_{28}$N$_4$O$_2$Na: H$_2$O Calcd.: 77.28%C, 4.58%H, 8.00%N, 6.86%O; Found: 75.90%C, 4.49%H, 7.81%N, 6.57%O.

N-p-nitrobenzyl-5-(p-(p-nitrobenzyl)carboxyphenyl)-10,15,20-triphenylporphyrin, (2)

Diphenyl-p-nitrobenzylsulfonium tetrafluoroborate and H$_2$CP$_3$P were combined in a 2:1 ratio in CH$_2$Cl$_2$ (typically, 110 mg and 100 mg, respectively, in 80 mL) and heated in a glass and Teflon pressure vessel at 110° C. for 2 h. After the vessel had cooled to room temperature, the solution was neutralized with 40 mL of 1M aqueous ammonia and extracted twice with 100 mL of water. Chromatography on neutral alumina with CH$_2$Cl$_2$ gave a trace of 5-p-(p-nitrobenzyl)carboxyphenyl)-10,15,20-triphenylporphine as the first band (pink) and the desired compound as the second band (green on the column, eluted as a purple solution). After crystallization from CH$_2$Cl$_2$ and CH$_3$CN, the yields are 85–90%. Visible-uv spectrum in CH$_2$Cl$_2$: 677 nm (3.69), 613 nm (3.70), 574 nm (4.18), 531 nm (3.98) and 436 nm (5.29). The ester carbonyl stretch is at 1702 cm$^{-1}$. Anal. for C$_{59}$H$_{40}$N$_6$O$_6$, Calcd.: 76.28% C, 4.34% H, 9.04% N, 10.33% O, Found: 76.35% C, 4.41%H, 8.90%N, 10.47%O.

N-p-nitrobenzyl-5-p-carboxyphenyl-10,15,20-tris(p-sulfophenyl)porphyrin bis(hydrogensulfate)hydrate sodium salt, (3)

Treatment of (2) with concentrated sulfuric acid on a steam bath overnight gave (3). The product was isolated by carefully adding water to the H$_2$SO$_4$ slurry (5 mL of H$_2$O to 250 mg of (2) in 20 mL H$_2$SO$_4$), causing precipitation of the dication as the bis(hydrogensulfate) salt. Precipitation was aided by addition of acetone (40 mL). The crude product was purified by the common procedure for sulfonated porphyrins, dissolution in methanol and reprecipitation with acetone, giving an 87% yield. Visible-uv spectrum in 1M NaOH and in pH 8.5 0.1M borate buffer: 677 nm (3.83), 594 nm (4.16), 544 nm (3.94), 436 nm (4.77) and 414 nm (4.72); in 0.05M HCl, 683 nm (4.47) and 450 nm (5.25). The carbonyl stretch for the sodium salt is at 1625 cm$^{-1}$. Anal. for C$_{45}$H$_{29}$N$_5$O$_4$.2HSO$_4$.3Na.18H$_2$O, Calcd. 38.99%C, 4.64%H, 4.37%N, 10.01%O, Found: 37.11%C, 3.64%H, 3.72%N, 11.30%S.

What is claimed is:

1. A process for the preparation of N-substituted porphyrins of the formula:

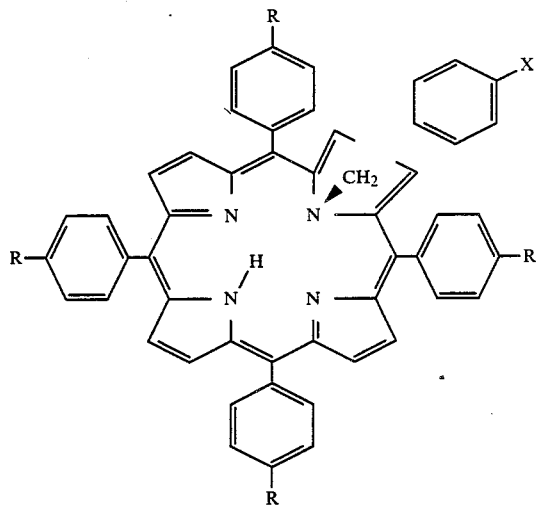

wherein X is hydrogen, hydroxy, nitro, lower alkyl or lower alkoxy and R is carboxy or sulfonato which comprises contacting a porphyrin compound with a benzyl diphenylsulfonium compound in the presence of an inert organic solvent.

2. The process according to claim 1 wherein the benzyl diphenylsulfonium compound is a benzyl diphenylsulfonium salt.

3. The process according to claim 2 wherein the salt is benzyldiphenylsulfonium tetrafluoroborate and the solvent is dichloromethane.

4. The process according to claim 1 wherein the porphyrin compound is 5,10,15,20-tetrakis(p-carboxyphenyl)porphyrin or 5-(p-carboxyphenyl)-10,15,20-tris(p-sulfophenyl)porphyrin.

5. The process according to claim 1 wherein the benzyl group of the benzyldiphenylsulfonium compound is unsubstituted or mono-substituted with hydroxy, nitro, lower alkyl or lower alkoxy.

6. The process according to claim 2 wherein the compound is a diphenyl-p-nitrobenzylsulfonium salt.

7. The process according to claim 2 wherein the salt is diphenyl-p-nitrobenzylsulfonium tetrafluoroborate.

8. A process for the preparation of N-benzylporphyrins which comprises contacting a naturally derived porphyrin with a benzyl diphenylsulfonium compound in the presence of an inert organic solvent.

9. The process according to claim 8 wherein the benzyl diphenylsulfonium compound is a benzyldiphenylsulfonium salt.

10. The process according to claim 9 wherein the salt is benzyldiphenylsulfonium tetrafluoroborate.

11. The process according to claim 8 wherein the porphyrin is hematoporphyrin, protoporphyrin or deuteroporphyrin.

12. N-benzylhematoporphyrin.

13. N-benzylprotoporphyrin.

14. N-benzyldeuteroporphyrin.

15. N-benzyl5,10,15,20-tetrakis(p-carboxyphenyl)-porphyrin.

16. N-p-nitrobenzyl-5-(p-carboxyphenyl)-10,15,20-tris(p-sulfophenyl)porphyrin.

* * * * *

UNITED STATES PATENT AND TRADEMARK OFFICE
CERTIFICATE OF CORRECTION

PATENT NO.   : 4,783,529
DATED        : November 8, 1988
INVENTOR(S)  : David Lavallee It is certified that error appears in the above-identified patent and that said Letters Patent is hereby corrected as shown below:

Column 1, line 12: "have" should read as --has--

Column 2, line 1: "hydrochlorice" should read as --hydrochloric--

Column 14, line 67: "of pH" should read as --to pH--

Column 15, line 18: "(1)" should read as --(1).--

Column 15, line 51: "(2)" should read as --(2).--

Column 16, line 6: "(3)" should read as --(3).--

Signed and Sealed this

Twenty-third Day of April, 1991

Attest:

HARRY F. MANBECK, JR.

Attesting Officer

Commissioner of Patents and Trademarks